(12) United States Patent
Li et al.

(10) Patent No.: US 12,150,482 B2
(45) Date of Patent: *Nov. 26, 2024

(54) ELECTRONIC CIGARETTE AND HEATING ASSEMBLY THEREOF

(71) Applicant: SHENZHEN SMOORE TECHNOLOGY LIMITED, Shenzhen (CN)

(72) Inventors: Xiaoping Li, Shenzhen (CN); Changyong Yi, Shenzhen (CN); Zhenlong Jiang, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 1016 days.

This patent is subject to a terminal disclaimer.

(21) Appl. No.: 16/969,800

(22) PCT Filed: Feb. 13, 2018

(86) PCT No.: PCT/CN2018/076692
§ 371 (c)(1),
(2) Date: Aug. 13, 2020

(87) PCT Pub. No.: WO2019/157648
PCT Pub. Date: Aug. 22, 2019

(65) Prior Publication Data
US 2021/0000181 A1  Jan. 7, 2021

(51) Int. Cl.
*A24F 40/46* (2020.01)
*A24F 40/44* (2020.01)
*A24F 40/10* (2020.01)

(52) U.S. Cl.
CPC .............. *A24F 40/46* (2020.01); *A24F 40/44* (2020.01); *A24F 40/10* (2020.01)

(58) Field of Classification Search
CPC .......... A24F 40/46; A24F 40/42; A24F 40/44; A24F 40/10; H05B 2203/021
See application file for complete search history.

(56) References Cited

U.S. PATENT DOCUMENTS 9,289,014 B2  3/2016  Tucker et al.
9,603,389 B2  3/2017  Chen
(Continued)

FOREIGN PATENT DOCUMENTS

CA   3022340 A1   11/2017
CN   103960782 A   8/2014
(Continued)

OTHER PUBLICATIONS

Supplementary European Search Report for EP Application No. 1890592.7 date Jul. 2, 2021.
(Continued)

*Primary Examiner* — Abdullah A Riyami
*Assistant Examiner* — Nader J Alhawamdeh
(74) *Attorney, Agent, or Firm* — Dorsey & Whitney LLP

(57) ABSTRACT

An electronic cigarette and a heating assembly thereof. The heating assembly comprises a porous member for absorbing an e-liquid and at least one heating member for heating and atomizing the e-liquid absorbed by the porous member. The at least one heating member comprises an elongated sheet-shaped heating portion. The sheet-shaped heating portion comprises a heating grid. At least part of the heating grid is partially embedded in the porous member. The porous member comprises an atomization surface corresponding to the at least part of the heating grid.

20 Claims, 14 Drawing Sheets

(56) References Cited

U.S. PATENT DOCUMENTS

| | | | |
|---|---|---|---|
| 9,795,168 B2* | 10/2017 | Zhu | A24F 40/46 |
| 9,814,269 B2 | 11/2017 | Li et al. | |
| 9,861,129 B2 | 1/2018 | Liu et al. | |
| 9,877,516 B2 | 1/2018 | Tucker et al. | |
| 10,687,557 B2 | 6/2020 | Tucker et al. | |
| 10,973,262 B2* | 4/2021 | Li | A24F 40/46 |
| 2015/0189919 A1 | 7/2015 | Liu | |
| 2016/0073692 A1 | 3/2016 | Alarcon et al. | |
| 2016/0106153 A1* | 4/2016 | Zhu | A24F 40/46 |
| | | | 392/404 |
| 2016/0143358 A1 | 5/2016 | Zhu | |
| 2016/0192707 A1 | 7/2016 | Li et al. | |
| 2016/0309785 A1 | 10/2016 | Holtz | |
| 2016/0353802 A1 | 12/2016 | Malgat et al. | |
| 2017/0105455 A1 | 4/2017 | Qiu | |
| 2017/0112193 A1 | 4/2017 | Chen | |
| 2017/0150755 A1* | 6/2017 | Batista | A24F 40/42 |
| 2017/0215481 A1 | 8/2017 | Li et al. | |
| 2017/0340012 A1 | 11/2017 | Mironov et al. | |
| 2017/0340015 A1 | 11/2017 | Thorens | |
| 2018/0035720 A1 | 2/2018 | Qiu | |
| 2018/0184714 A1 | 7/2018 | Liu | |
| 2019/0046745 A1 | 2/2019 | Nettenstrom et al. | |
| 2019/0099562 A1 | 4/2019 | Nettenstrom et al. | |
| 2019/0350236 A1 | 11/2019 | Tian | |
| 2019/0350263 A1 | 11/2019 | Qiu | |
| 2019/0364972 A1* | 12/2019 | Lin | A24F 40/40 |
| 2020/0260787 A1 | 8/2020 | Zinovik et al. | |
| 2020/0352238 A1 | 11/2020 | Simpson et al. | |
| 2020/0367564 A1* | 11/2020 | Li | A24F 40/44 |
| 2020/0397043 A1* | 12/2020 | Li | A24F 40/44 |
| 2021/0000179 A1* | 1/2021 | Li | A24F 40/46 |
| 2021/0000181 A1* | 1/2021 | Li | A24F 40/46 |

FOREIGN PATENT DOCUMENTS

| | | |
|---|---|---|
| CN | 203851804 U | 10/2014 |
| CN | 204070542 U | 1/2015 |
| CN | 104522891 A | 4/2015 |
| CN | 104824853 A | 8/2015 |
| CN | 204796739 U | 11/2015 |
| CN | 204949517 U | 1/2016 |
| CN | 105310114 A | 2/2016 |
| CN | 105394816 A | 3/2016 |
| CN | 105433446 A | 3/2016 |
| CN | 205106385 U | 3/2016 |
| CN | 105768229 A | 7/2016 |
| CN | 205512338 U | 8/2016 |
| CN | 205624481 U | 10/2016 |
| CN | 106136327 A | 11/2016 |
| CN | 205695698 U | 11/2016 |
| CN | 205813574 U | 12/2016 |
| CN | 206062123 U | 4/2017 |
| CN | 206062138 U | 4/2017 |
| CN | 206079042 U | 4/2017 |
| CN | 106723372 A | 5/2017 |
| CN | 106820269 A | 6/2017 |
| CN | 106820272 A | 6/2017 |
| CN | 206260849 U | 6/2017 |
| CN | 206390306 U | 8/2017 |
| CN | 206507320 U | 9/2017 |
| CN | 206518143 U | 9/2017 |
| CN | 206525553 U | 9/2017 |
| CN | 206729208 U | 12/2017 |
| CN | 206729211 U | 12/2017 |
| CN | 206808661 U | 12/2017 |
| CN | 207978957 U | 10/2018 |
| CN | 207978958 U | 10/2018 |
| CN | 207978959 U | 10/2018 |
| CN | 208048028 U | 11/2018 |
| CN | 208113970 U | 11/2018 |
| EP | 2574247 A1 | 4/2013 |
| EP | 2946678 A1 | 11/2015 |
| EP | 3020292 A1 | 5/2016 |
| EP | 3099190 A1 | 12/2016 |
| EP | 3162778 A1 | 5/2017 |
| EP | 3188570 A2 | 7/2017 |
| EP | 3200559 A2 | 8/2017 |
| EP | 3569072 A1 | 11/2019 |
| EP | 3524069 B1 | 12/2022 |
| GB | 2504074 A | 1/2014 |
| JP | 2007117970 A | 5/2007 |
| WO | 2014019024 A1 | 2/2014 |
| WO | 2014079024 A1 | 5/2014 |
| WO | 2014151040 A2 | 9/2014 |
| WO | 2016107767 A1 | 7/2016 |
| WO | 2016119170 A1 | 8/2016 |
| WO | 2016154792 A1 | 10/2016 |
| WO | 2016161554 A1 | 10/2016 |
| WO | 2016169115 A1 | 10/2016 |
| WO | 2016198417 A1 | 12/2016 |
| WO | 2017005471 A1 | 1/2017 |
| WO | 2017163050 A1 | 9/2017 |
| WO | 2017163051 A1 | 9/2017 |
| WO | 2017163052 A1 | 9/2017 |
| WO | 2017187148 A1 | 11/2017 |
| WO | 2018007965 A1 | 1/2018 |
| WO | 2018019485 A1 | 2/2018 |
| WO | 2018172765 A1 | 9/2018 |

OTHER PUBLICATIONS

Extended European Search Report for European Patent Application No. 22212991.8 mailed Apr. 5, 2023.
Extended European Search Report for European Patent Application No. 23157027.6 mailed Apr. 5, 2023.
Notice of Allowance for U.S. Appl. No. 17/189,904 mailed Jun. 15, 2023.
International Search Report from PCT Application No. PCT/CN2018/076692 mailed Oct. 25, 2018.
Decision of Rejection for Chinese Application No. 201810150549.7 mailed Apr. 20, 2020.
First Office Action for Chinese Application No. 201810150549.7 mailed Mar. 22, 2019.
Notification of Reexamination for Chinese Application No. 201810150549.7 mailed Nov. 5, 2021.
Second Office Action for Chinese Application No. 201810150549.7 mailed Dec. 25, 2019.
Written Opinion for International Application No. PCT/CN2018/076692 mailed Oct. 25, 2018.
European Office Action dated Apr. 30, 2021 for EP181745035.
European Office Action dated Dec. 3, 2021 for EP181745035.
European Search Report dated Jan. 4, 2019 for EP18174503.5.
Evaluation Report dated Feb. 13, 2018 for CN2018202606170.
International Search Report and Written Opinion dated Sep. 20, 2018 for PCT/CN2018/076694.
Notification of Grant dated Dec. 10, 2019 for CN2018101506907.
Office Action Aug. 14, 2019 for CN20180101506907.
Office Action dated Feb. 14, 2023 for U.S. Appl. No. 17/196,971.
Office Action dated Feb. 15, 2023 for U.S. Appl. No. 17/198,511.
Office Action dated Feb. 15, 2023 for U.S. Appl. No. 17/199,828.
Office Action dated Mar. 27, 2019 for CN2018101506907.
Office Action dated Dec. 23, 2022 for U.S. Appl. No. 17/189,904.
Communication Pursuant to Article 94(3) EPC for European Application No. 18905927.2 mailed Jul. 19, 2023.
Communication Pursuant to Article 94(3) EPC for European Application No. 18906621.0 mailed Jul. 20, 2023.
Non-Final Office Action for U.S. Appl. No. 16/969,653 mailed Aug. 11, 2023.
Non-Final Office Action for U.S. Appl. No. 16/969,800 mailed Aug. 14, 2023.
Non-Final Office Action for U.S. Appl. No. 16/969,828 mailed Aug. 30, 2023.
Notice of Allowance for U.S. Appl. No. 17/196,971 mailed Jun. 30, 2023.
Notice of Allowance for U.S. Appl. No. 17/198,511 mailed Jul. 28, 2023.

(56) References Cited

OTHER PUBLICATIONS

Notice of Allowance for U.S. Appl. No. 17/199,828 mailed Aug. 1, 2023.
Communication of Notices of Opposition for European Application No. 18174503.5 mailed Sep. 28, 2023.
First Notice of Opposition for European Application No. 18174503.5 mailed Sep. 19, 2023.
Notice of Allowance for U.S. Appl. No. 16/969,686 mailed Oct. 3, 2023.
Second Notice of Opposition for European Application No. 18174503.5 mailed Sep. 19, 2023.
Decision for Reexamination for Chinese Application No. 201810150549.7 mailed Mar. 31, 2022.
Decision of Reexamination for Chinese Application No. 201810150539.3 mailed Jul. 16, 2020.
Decision of Reexamination for Chinese Application No. 201810150560.3 mailed Jul. 16, 2020.
Decision of Reexamination for Chinese Application No. 201810150677.1 mailed Apr. 8, 2022.
Decision of Rejection for Chinese Application No. 201810150539.3 mailed Mar. 19, 2020.
Decision of Rejection for Chinese Application No. 201810150560.3 mailed Mar. 19, 2020.
Decision of Rejection for Chinese Application No. 201810150677.1 mailed Apr. 22, 2020.
Extended European Search Report for European Application No. 18906272.2 mailed Aug. 6, 2021.
Extended European Search Report for European Application No. 18906379.5 mailed Aug. 10, 2021.
Extended European Search Report for European Application No. 18906621.0 mailed Jul. 12, 2021.
Final Office Action for U.S. Appl. No. 16/969,828 mailed Jan. 25, 2024.
First Office Action for Chinese Application No. 201810150539.3 mailed Mar. 22, 2019.
First Office Action for Chinese Application No. 201810150560.3 mailed Mar. 25, 2019.
First Office Action for Chinese Application No. 201810150677.1 mailed Mar. 25, 2019.
International Search Report and Written Opinion for Internation Application No. PCT/CN/2018/076695 mailed Oct. 23, 2018.
International Search Report and Written Opinion from International Application No. PCT/CN2018/076688 mailed Sep. 10, 2018.
International Search Report and Written Opinion from International Application No. PCT/CN2018/076691 mailed Oct. 18, 2018.
Notice of Allowance for U.S. Appl. No. 16/969,653 mailed Feb. 20, 2024.
Notice of Allowance for U.S. Appl. No. 16/969,828 mailed May 1, 2024.
Notice of Grant for Chinese Application No. 201810150539.3 mailed Aug. 24, 2020.
Notice of Grant for Chinese Application No. 201810150549.7 mailed Apr. 28, 2022.
Notice of Grant for Chinese Application No. 201810150560.3 mailed Aug. 13, 2020.
Notice of Grant for Chinese Application No. 201810150677.1 mailed Apr. 21, 2022.
Notification of Reexamination for Chinese Application No. 201810150677.1 mailed Nov. 5, 2021.
Second Office Action for Chinese Application No. 201810150539.3 mailed Sep. 27, 2019.
Second Office Action for Chinese Application No. 201810150560.3 mailed Dec. 25, 2019.
Second Office Action for Chinese Application No. 201810150677.1 mailed Nov. 26, 2019.

* cited by examiner

ELECTRONIC CIGARETTE AND HEATING ASSEMBLY THEREOF

TECHNICAL FIELD

The present disclosure relates to smoking products, and more particularly, to an electronic cigarette and a heating assembly thereof.

BACKGROUND

Electronic cigarettes are also known as virtual cigarettes or electronic atomizers. Electronic cigarettes are used as substitutes for cigarette products and are often used for quitting smoking. The electronic cigarettes have similar appearance and flavor to cigarette products, but generally are free of harmful chemicals such as tar, aerosol, or the like in the cigarettes. The electronic cigarette mainly includes an atomizer and a power supply assembly. At present, the atomizer of the electronic cigarette mostly includes a capillary structure for guiding liquid and a heating element cooperating with the capillary structure, which can meet the needs for atomization to a certain extent. However, such a heating element may have a problem of uneven heating during heating, as a result, the e-liquid is atomized at different temperatures and the mouthfeel of the smoke is poor. Moreover, if the temperature of a certain portion of the heating element is too high, it will cause the e-liquid to decompose into toxic substances and endanger the health of the user.

SUMMARY

The technical problem to be solved by the present disclosure is to provide an improved electronic cigarette and a heating assembly thereof.

The technical solution used in the present disclosure to solve one of the technical problems is: a heating assembly of an electronic cigarette is provided, which includes a porous body configured for adsorbing e-liquid and at least one heating element configured for heating and atomizing the e-liquid adsorbed into the porous body. The at least one heating element includes an elongated sheet heating portion. The sheet heating portion includes a heating net, and at least partial section of the heating net is at least partially embedded in the porous body, and the porous body includes an atomizing surface corresponding to the at least partial section.

In some embodiments, a density of meshes of the at least partial section in a length direction is less in the middle and greater at both sides, and changes gradually or stepwise.

In some embodiments, a density of meshes of the at least partial section in a length direction is greater in the middle and less at both sides, and changes gradually or stepwise.

In some embodiments, a density of meshes of the at least partial section in a width direction is less at one side and greater at the other side, and changes gradually or stepwise.

In some embodiments, the at least partial section is embedded in the porous body with a width direction thereof following along a movement direction of the e-liquid and/or smoke in the porous body.

In some embodiments, the at least partial section in the width direction thereof is substantially perpendicular to a plane where the atomizing surface is located.

In some embodiments, the at least partial section extends in a length direction thereof along a direction parallel to a plane where the atomizing surface is located.

In some embodiments, the porous body includes a receiving groove adapted to the at least partial section, the receiving groove is formed on the atomizing surface, and a depth direction of the receiving groove is substantially perpendicular to a plane where the atomizing surface is located.

In some embodiments, the at least partial section is received in the receiving groove, and a top surface of the at least partial section is flush with the atomizing surface, or the top surface thereof is lower than the atomizing surface, or the top surface thereof protrudes from the atomizing surface.

In some embodiments, two opposite surfaces of the at least partial section defined by length and width are in direct contact with the porous body.

In some embodiments, the porous body includes a sintered porous body, the at least partial section is integrally formed with the sintered porous body by sintering.

In some embodiments, the at least partial section includes a plurality of flat portions parallel to each other and a plurality of bending portions sequentially connecting the plurality of flat portions in series, the flat portions are arranged at intervals in a direction parallel to a plane where the atomizing surface is located, and the intervals are larger in the middle and smaller at both sides, or smaller in the middle and larger at the both sides.

In some embodiments, the at least partial section includes a plurality of flat portions parallel to each other and a plurality of bending portions sequentially connecting the plurality of flat portions in series, the atomizing surface is provided in a wavy shape, and the plurality of flat portions are disposed corresponding to troughs of the atomizing surface, respectively.

In some embodiments, the porous body includes a first layer adjacent to the atomizing surface and a second layer away from the atomizing surface. A thermal conductivity of the first layer is greater than that of the second layer.

In some embodiments, the at least partial section is embedded in the first layer.

In some embodiments, a thermal conductivity of the porous body gradually increases in a direction from an area away from the atomizing surface to an area adjacent to the atomizing surface.

In some embodiments, the at least partial section is adjacent to the atomizing surface.

In some embodiments, the at least partial section is integrally embedded in the porous body.

In some embodiments, the at least one heating element includes two electrical connecting portions integrally connected to both ends of the sheet heating portion, respectively; each of the electrical connecting portions includes a lower portion protruding from a lower edge of the sheet heating portion and an upper portion protruding from an upper edge of the sheet heating portion.

An electronic cigarette is provided which includes the heating assembly of the electronic cigarette in any one of the embodiments described above.

Beneficial Effect

The present disclosure has the beneficial effects that, by adjusting the distribution of the meshes, some heat accumulation problems in the electronic cigarette can be handled very easily, so that the heat distribution can better meet the needs of the design thereof.

BRIEF DESCRIPTION OF THE DRAWINGS

The present disclosure will be further described below with reference to the accompanying drawings and embodiments, in the drawings.

DETAILED DESCRIPTION OF THE EMBODIMENTS

For clearer understanding of the technical features, objects, and effects of the present disclosure, the specific embodiments of the present disclosure will be described in detail with reference to the accompanying drawings.

Figure 1:
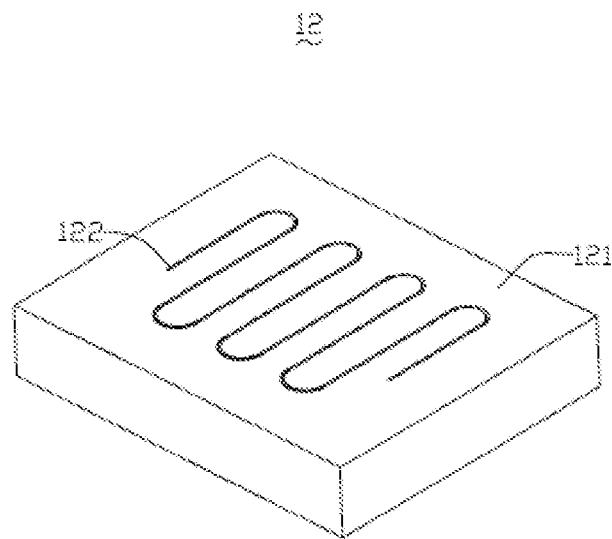
FIG. 1 is a schematic three-dimension assembled view of a heating assembly in accordance with some embodiments of the present disclosure.
Figure 2:
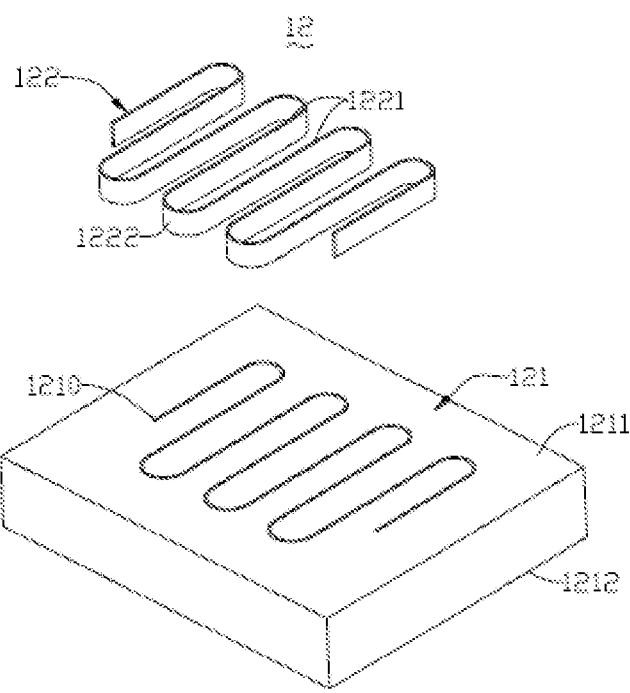
FIG. 2 is a schematic three-dimension exploded view of the heating assembly of FIG. 1.
Figure 3:
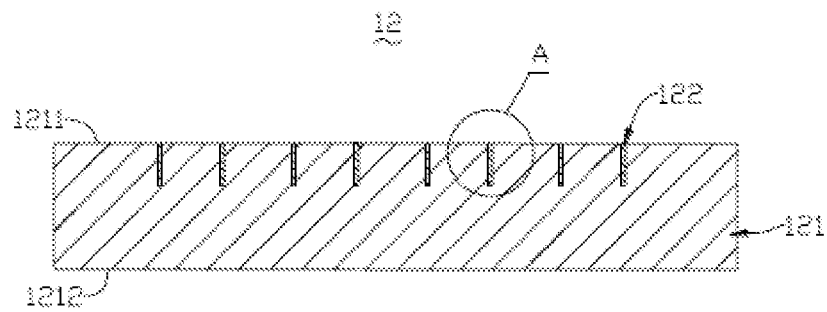
FIG. 3 is a schematic longitudinal sectional view of the heating assembly of FIG. 1.

FIG. 1 to FIG. 3 illustrate a heating assembly 12 of an electronic cigarette in some embodiments of the present disclosure. The heating assembly 12 can be applied in an atomizer of the electronic cigarette to heat and atomize e-liquid. The heating assembly 12 may include a porous body 121 for adsorbing the e-liquid from a liquid storage cavity of the atomizer and a heating element 122 for heating and atomizing the e-liquid adsorbed into the porous body 121. The heating element 122 includes an elongated sheet heating portion which is embedded in the porous body 121, so that all or most of a surface area of the sheet heating portion is in contact with the porous body 121, which brings effects such as high atomization efficiency, low loss of heat, prevention or great reduction of dry burning and so on.

Preferably, the sheet heating portion is embedded in the porous body 121 in such a manner that a movement direction of the e-liquid and/or smoke in the porous body 121 follows along a width direction of the sheet heating portion, so that the movement of the e-liquid and/or the smoke can be smoother on one hand, and more heat can be concentrated near an atomizing surface 1211 instead of being transferred towards a liquid adsorbing surface 1212 along an opposite direction on the other hand, so as to improve the utilization of the heat. The porous body 121, in some embodiments, can be made of hard capillary structures such as porous ceramics, porous glass ceramics, porous glass, and so on. The sheet heating portion of the heating element 122, in some embodiments, can be made of stainless steel, nickel-chromium alloy, iron-chromium-aluminum alloy, titanium and so on.

When the porous body 121 has a sintered structure, the sheet heating portion of the heating element 122 can be integrally formed with the porous body 121 by sintering. Specifically, in an example that the porous body 121 is made of the porous ceramics, when the sheet heating portion is a metal sheet, a green body of the porous body 121 can be first formed using the Kaolin clay mass, and then the sheet heating portion of the heating element 122 can be embedded into the green body, which can be baked and sintered thereafter. When the sheet heating portion is a coated sheet heating portion, the sheet heating portion can be first coated on an organic film, and then the organic film coated with the sheet heating portion is inserted into the green body, which is baked and sintered thereafter. The organic film is burnt off in the sintering process, and only the coated sheet heating portion is tightly coupled with the porous body.

Compared with a heating wire, the sheet heating portion has a larger specific surface area. When certain mechanical properties are satisfied, the thickness of the sheet heating portion can be greatly smaller than the diameter of the heating wire (the heating wire with too small diameter is easy to break). Therefore, the sheet heating portion can be made very thin to lead to low internal accumulation of heat and high atomization efficiency. For example, in some embodiments, the sheet heating portion can have a thickness of 0.04 mm to 0.1 mm and a width of 0.3 mm to 0.6 mm. In some cases, the thickness of the sheet heating portion can be even smaller, for example, about 0.008 mm.

As shown in the figures, the porous body 121 can be substantially, but not limited to, in a shape of a cuboid in some embodiments. The porous body 121 includes the atomizing surface 1211 and the liquid adsorbing surface 1212 parallel to the atomizing surface 1211. The liquid adsorbing surface 1212 is used to be in communication with the liquid storage cavity such that the e-liquid can flow into the porous body 121. The e-liquid is heated and atomized in the porous body 121 and then escapes through the atomizing surface 1211. The porous body 121 includes a receiving groove 1210 for receiving the sheet heating portion of the heating element 122. The receiving groove 1210 extends, in a length direction, along a direction parallel to a plane where the atomizing surface 1211 is located, and extends, in a depth direction, along a direction away from the atomizing surface 1211.

In some embodiments, since the liquid adsorbing surface 1212 and the atomizing surface 1211 are parallel to each other, the movement directions of the e-liquid and the smoke in the porous body 121 are both perpendicular to the atomizing surface 1211. The receiving groove 1210, in the depth direction thereof, is perpendicular to the plane where the atomizing surface 1211 is located, so that when the sheet heating portion of the heating element 122 is received therein, the sheet heating portion of the heating element 122, in the width direction thereof, is also perpendicular to the plane where the atomizing surface 1211 is located. When the sheet heating portion of the heating element 122 in the width direction thereof is perpendicular to the atomizing surface 1211, on one hand, the movement of the smoke and the e-liquid in the porous body 121 will be smoother, and on the other hand, the manufacturing of the heating element 122 is more convenient. In addition, the main heat-conducting surfaces (that is, the front surface and the rear surface defined by the length and width) of the sheet heating portion of the heating element 122 are located in the lateral direction to heat the e-liquid near the atomizing surface 1211 and thus improve the atomization efficiency. Furthermore, since the sheet heating portion of the heating element 122 is relatively thin, and an upper surface and a lower surface defined by the thickness and the length are both small, the e-liquid away from the atomizing surface 1211 adsorbs less heat, which can reduce the waste of heat and save energy.

It can be understood that the sheet heating portion of the heating element 122 is not limited to one having the width direction perpendicular to the plane where the atomizing surface 1211 is located. In some embodiments, it is preferable to be slightly inclined, that is, the sheet heating portion of the heating element 122 is substantially perpendicular to the atomizing surface 1211122. Preferably, an angle between the width direction of the sheet heating portion of the heating element 122 and a normal direction of the atomizing surface 1211 is within 20 degrees.

It can further be understood that the sheet heating portion of the heating element 122 is not limited to a unique corresponding relationship that the heating portion is substantially perpendicular in its whole section in the entire length to the plane where the atomizing surface 1211 is located. Some advantages disclosed in the embodiments can be obtained as long as some sections of the heating portion satisfies such relationship. Preferably, at least half or more of the heating portion satisfies such relationship.

It can be understood that, in some embodiments, if the movement direction of the e-liquid and/or the smoke in the porous body 121 is not perpendicular to the plane where the atomizing surface 1211 is located, the arrangement of the sheet heating portion of the heating element 122 may preferably be adjusted accordingly such that the width direction of the sheet heating portion is parallel to or follows along the movement direction of the e-liquid and/or the smoke in the porous body 121 as much as possible.

In some embodiments, in order to make the heat distribution more uniform, the sheet heating portion of the heating element 122 need to be distributed uniformly in the porous body 121 near the atomizing surface 1211 as much as possible. In some embodiments, the sheet heating portion of the heating element 122 can be provided in an S-shape in the length direction, which includes a plurality of flat portions 1221 arranged in parallel with each other at equal intervals, and a plurality of bending portions 1222 connecting the plurality of flat portions 1221 together in series. Correspondingly, the receiving groove 1210 is also provided in an S-shape, and the size of which is adapted to the size of the sheet heating portion of the heating element 122, so that the sheet heating portion of the heating element 122 can be better received therein and the receiving groove 1210 is in close contact with the sheet heating portion of the heating element 122. It can be understood that the sheet heating portion of the heating element 122 is not limited to be provided in the S-shape, and can also be provided in other shapes such as a flat strip shape, a tape shape, and a wavy shape as required. In addition, it is not limited that only one sheet heating portion of the heating element 122 is provided in one porous body 121, two or more heating elements 122 may also be provided.

Figure 4:
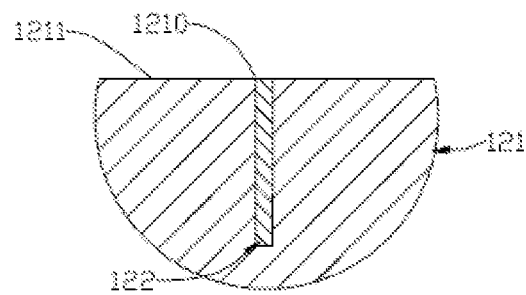
FIG. 4 is a schematic partial enlarged view of a portion A of the heating assembly of FIG. 3.

As shown in FIG. 4, in some embodiments, the width of the sheet heating portion of the heating element 122 is equal to the depth of the receiving groove 1210. When the sheet heating portion of the heating element 122 is received in the receiving groove 1210 along the width direction, a top surface of the sheet heating portion is flush with the atomizing surface 1211, that is, the plane where the sheet heating portion of the heating element 122 is located is parallel to the atomizing surface 1211. Since the top surface (an upper surface defined by the length and thickness) of the sheet heating portion of the heating element 122 is exposed to the outside, the heating assembly 12 can atomize the e-liquid near the top surface more quickly, and the advantages of quick smoke generation and convenient manufacturing are provided.

In some embodiments, a thermal conductivity of the porous body 121 is uniform in a direction from the liquid adsorbing surface 1212 to the atomizing surface 1211. In other embodiments, the thermal conductivity of the porous body 121 gradually increases in the direction from the liquid adsorbing surface 1212 to the atomizing surface 1211. As a result, the e-liquid in the porous body 121 is atomized more quickly as getting closer to the atomizing surface 1211, therefore, the movement of the e-liquid towards the atomizing surface 1211 is accelerated to improve the atomization efficiency.

In addition, the sheet heating portion of the heating element 122 is embedded in the porous body 121 along the width direction, the sheet heating portion of the heating element 122 has a large contact area with the porous body 121, thus, the heating efficiency is high and the coupling is firm and uneasy to shed off. Further, such a configuration allow the sheet heating portion of the heating element 122 to be as thin as possible, and the exposed portion of the sheet heating portion of the heating element 122 is relatively narrow, which can therefore greatly reduce the occurrence of dry burning of the exposed portion.

Figure 5:
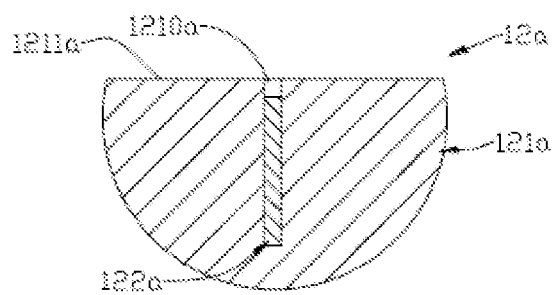
FIG. 5 is a schematic partial enlarged view of a portion A in a first alternative solution of the heating assembly of FIG. 1.

FIG. 5 illustrates a heating assembly 12*a* in some embodiments of the present disclosure. As an alternative solution for the heating assembly 12 mentioned above, the heating assembly 12*a* is different from the heating assembly 12 mainly in that a width of a sheet heating portion of a heating element 122*a* is smaller than a depth of a receiving groove 1210*a*, as a result, when the sheet heating portion of the heating element 122*a* is received in the receiving groove 1210*a* along a width direction, a top surface of the sheet heating portion is lower than an atomizing surface 1211*a*. Such configuration can allow for accumulation of the e-liquid in a slot channel between the top surface and the atomizing surface 1211*a*, avoiding the exposure of the top surface and further reducing dry burning.

Figure 6:
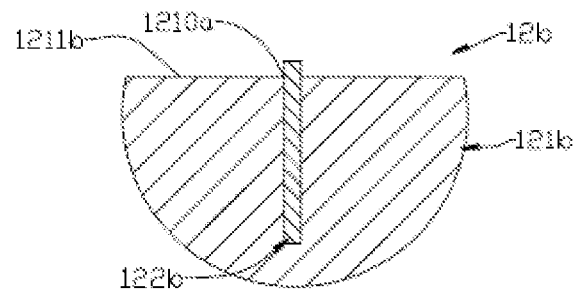
FIG. 6 is a schematic partial enlarged view of a portion A in a second alternative solution of the heating assembly of FIG. 1.

FIG. 6 illustrates a heating assembly 12*b* in some embodiments of the present disclosure. As an alternative solution for the heating assembly 12 mentioned above, the heating assembly 12*b* is different from the heating assembly 12 mainly in that a width of a sheet heating portion of a heating element 122*b* is greater than a depth of a receiving groove 1210*b*, as a result, when the sheet heating portion of the heating element 122*b* is received in the receiving groove 1210*b* along a width direction, a top surface of the sheet heating portion protrudes from an atomizing surface 1211*b*. With such configuration, multiple atomization temperatures can be provided to achieve the effect of diversified mouthfeel, so as to meet the needs of different users.

Figure 7:
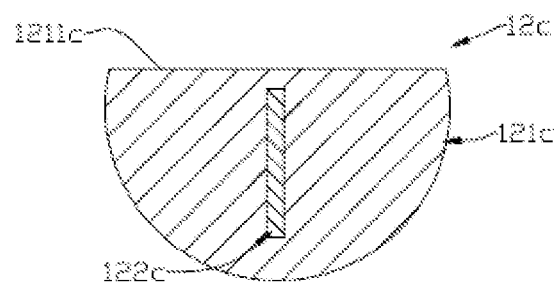
FIG. 7 is a schematic partial enlarged view of a portion A in a third alternative solution of the heating assembly of FIG. 1.

FIG. 7 illustrates a heating assembly 12*c* in some embodiments of the present disclosure. As an alternative solution for the heating assembly 12 mentioned above, the heating assembly 12*c* is different from the heating assembly 12 mainly in that a sheet heating portion of a heating element 122*c*, in a width direction thereof, is perpendicular to an atomizing surface 1211*c*, and the sheet heating portion is totally embedded into a porous body 121*c*. With such configuration, the occurrence of dry burning of the heating element 122*c* can be avoided.

Figure 8:
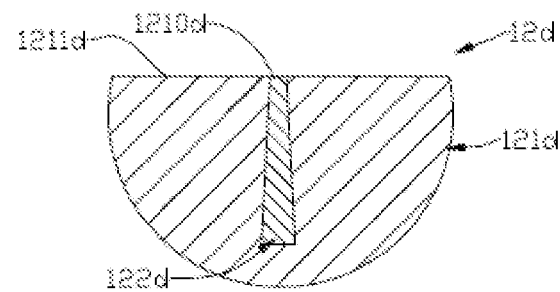
FIG. 8 is a schematic partial enlarged view of a portion A in a fourth alternative solution of the heating assembly of FIG. 1.

FIG. 8 illustrates a heating assembly 12*d* in some embodiments of the present disclosure. A width of a sheet heating portion of a heating element 122*d* is equal to a depth of a receiving groove 1210*d*, and when the sheet heating portion of the heating element 122*d* is received in the receiving groove 1210*d* along a width direction, a top surface of the sheet heating portion is flush with an atomizing surface 1211*d*. As an alternative solution for the heating assembly 12 mentioned above, it is different from the heating assembly 12 mainly in that a thickness of the sheet heating portion of the heating element 122*d* gradually increases along a depth direction of the receiving groove 1210*d*, such that a resistance of the sheet heating portion of the heating element 122*d* gradually decreases along the depth direction of the receiving groove 1210*d*.

Figure 9:
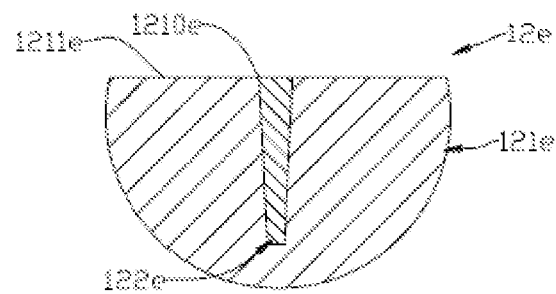
FIG. 9 is a schematic partial enlarged view of a portion A in a fifth alternative solution of the heating assembly of FIG. 1.

FIG. 9 illustrates a heating assembly 12*e* in some embodiments of the present disclosure. A width of a sheet heating portion of a heating element 122*e* is equal to a depth of a receiving groove 1210*e*, when the sheet heating portion of the heating element 122*e* is received in the receiving groove 1210*e* along a width direction, a top surface of the sheet heating portion is flush with an atomizing surface 1211*e*. As an alternative solution for the heating assembly 12 mentioned above, it is different from the heating assembly 12 mainly in that a thickness of the sheet heating portion of the heating element 122*e* gradually decreases along a depth direction of the receiving groove 1210*e*, such that a resistance of the sheet heating portion of the heating element 122*e* gradually increases along the depth direction of the receiving groove 1210*e*.

Figure 10:
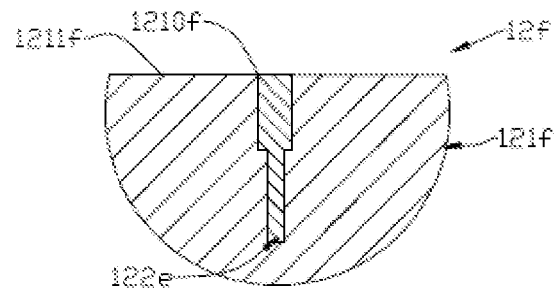
FIG. 10 is a schematic partial enlarged view of a portion A in a sixth alternative solution of the heating assembly of FIG. 1.

FIG. 10 illustrates a heating assembly 12*f* in some embodiments of the present disclosure. A width of a sheet heating portion of a heating element 122*f* is equal to a depth of a receiving groove 1210*f*, when the sheet heating portion of the heating element 122*f* is received in the receiving groove 1210*f* along a width direction, a top surface of the sheet heating portion is flush with an atomizing surface 1211*f*. As an alternative solution for the heating assembly 12 mentioned above, it is different from the heating assembly 12 mainly in that a thickness of a portion of the sheet heating portion of the heating element 122*f* adjacent to the atomizing surface 1211*f* is greater than a thickness of a portion thereof away from the atomizing surface 1211*f*, that is, the sheet heating portion of the heating element 122*f* has a stepped thickness. As a result, a resistance of the portion of the sheet heating portion of the heating element 122*f* adjacent to the atomizing surface 1211*f* is greater than a resistance of the portion thereof away from the atomizing surface 1211*f*.

Figure 11:
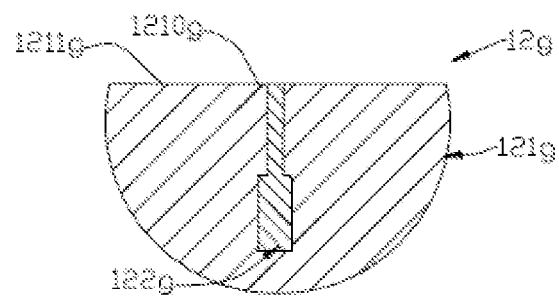
FIG. 11 is a schematic partial enlarged view of a portion A in a seventh alternative solution of the heating assembly of FIG. 1.

FIG. 11 illustrates a heating assembly 12*g* in some embodiments of the present disclosure. A width of a sheet heating portion of a heating element 122*g* is equal to a depth of a receiving groove 1210*g*, when the sheet heating portion of the heating element 122*g* is received in the receiving groove 1210*g* along a width direction, a top surface of the sheet heating portion is flush with an atomizing surface 1211*g*. As an alternative solution for the heating assembly 12 mentioned above, it is different from the heating assembly 12 mainly in that a thickness of a portion of the sheet heating portion of the heating element 122*g* adjacent to the atomizing surface 1211*g* is smaller than a thickness of a portion thereof away from the atomizing surface 1211*g*. As a result, a resistance of the portion of the sheet heating portion of the heating element 122*g* adjacent to the atomizing surface 1211*g* is lower than a resistance of the portion thereof away from the atomizing surface 1211*g*.

Figure 12:
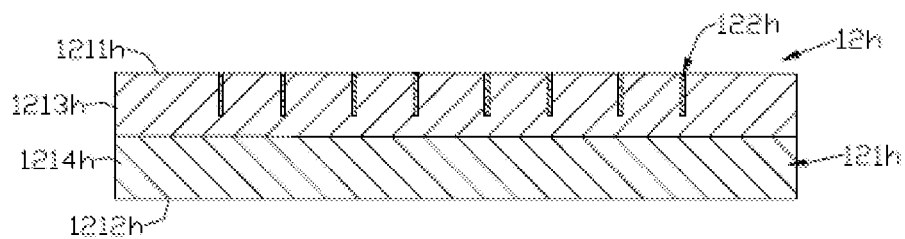
FIG. 12 is a schematic longitudinal sectional view of an eighth alternative solution of the heating assembly of FIG. 1.

FIG. 12 illustrates a heating assembly 12*h* in some embodiments of the present disclosure. A width of a sheet heating portion of a heating element 122*h* is equal to a depth of a receiving groove 1210*h*, when the sheet heating portion of the heating element 122*h* is received in the receiving groove 1210*h* along a width direction, a top surface of the sheet heating portion is flush with an atomizing surface 1211*h*. As an alternative solution for the heating assembly 12 mentioned above, it is different from the heating assembly 12 mainly in that a porous body 121*h* includes a first layer 1213*h* adjacent to the atomizing surface 1211*h* and a second layer 1214*h* away from the atomizing surface 1211*h*, and a thermal conductivity of the first layer 1213*h* is greater than that of the second layer 1214h, so that the heat in the portion adjacent to 1211h can be transferred faster, resulting in better atomization efficiency.

Figure 13:
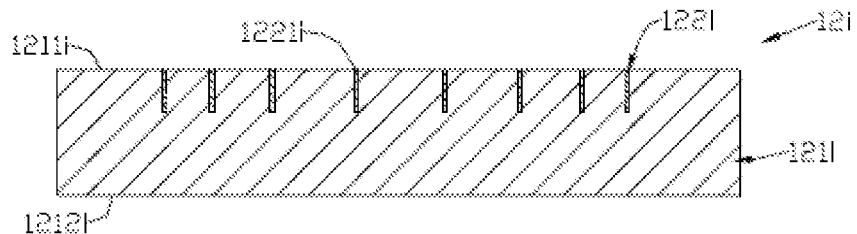
FIG. 13 is a schematic longitudinal sectional view of a ninth alternative solution of the heating assembly of FIG. 1.

FIG. 13 illustrates a heating assembly 12i in some embodiments of the present disclosure. A width of a sheet heating portion of a heating element 122i is equal to a depth of a receiving groove 1210i, when the sheet heating portion of the heating element 122i is received in the receiving groove 1210i along a width direction, a top surface of the sheet heating portion is flush with an atomizing surface 1211i. As an alternative solution for the heating assembly 12 mentioned above, it is different from the heating assembly 12 mainly in that flat portions 1221i of the sheet heating portion of the heating element 122i are arranged at intervals in a direction parallel to a plane where the atomizing surface is located, and the intervals are larger in the middle and smaller at both sides, so that the heating is more uniform. It can be understood that, in some embodiments, the flat portions 1221i of the sheet heating portion of the heating element 122i are arranged at intervals in the direction parallel to the plane where the atomizing surface is located, and the intervals are smaller in the middle and larger at the both sides.

Figure 14:
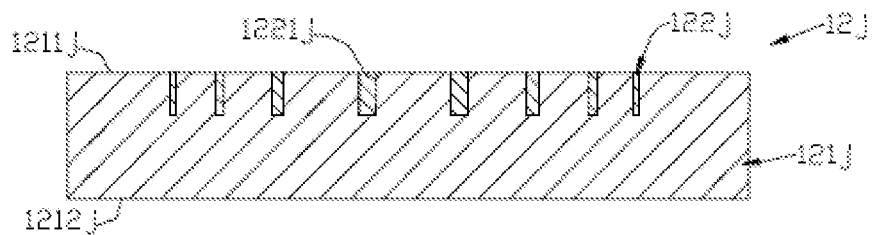
FIG. 14 is a schematic longitudinal sectional view of a tenth alternative solution of the heating assembly of FIG. 1.

FIG. 14 illustrates a heating assembly 12j in some embodiments of the present disclosure. A width of a sheet heating portion of a heating element 122j is equal to a depth of a receiving groove 1210j, when the sheet heating portion of the heating element 122j is received in the receiving groove 1210j along a width direction, a top surface of the sheet heating portion is flush with an atomizing surface 1211j. As an alternative solution for the heating assembly 12 mentioned above, it is different from the heating assembly 12 mainly in that flat portions 1221j of the sheet heating portion of the heating element 122j are thicker in the middle and thinner at both sides in a direction parallel to a plane where the atomizing surface is located.

Figure 15:
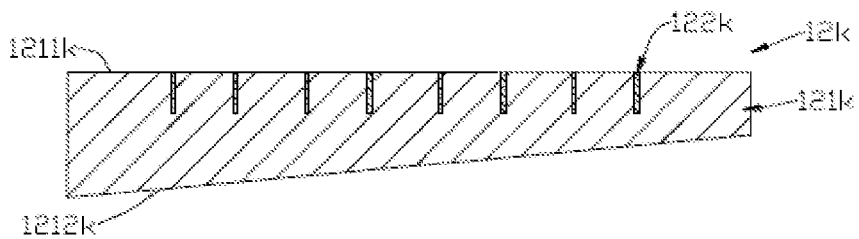
FIG. 15 is a schematic longitudinal sectional view of an eleventh alternative solution of the heating assembly of FIG. 1.

FIG. 15 illustrates a heating assembly 12k in some embodiments of the present disclosure. A width of a sheet heating portion of a heating element 122k is equal to a depth of a receiving groove 1210k, when the sheet heating portion of the heating element 122k is received in the receiving groove 1210k along a width direction, a top surface of the sheet heating portion is flush with an atomizing surface 1211k. As an alternative solution for the heating assembly 12 mentioned above, it is different from the heating assembly 12 mainly in that a liquid adsorbing surface 1212k is not parallel to the atomizing surface 1211k, so that the porous body 121k is in a trapezoidal shape.

Figure 16:
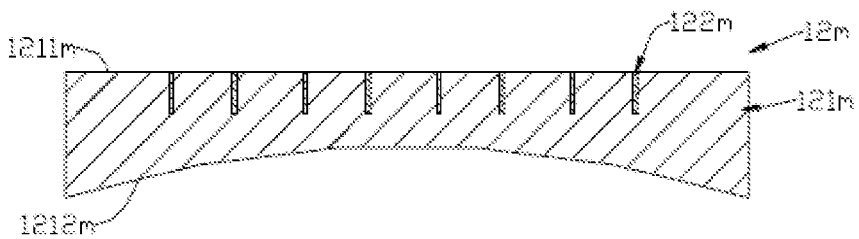
FIG. 16 is a schematic longitudinal sectional view of a twelfth alternative solution of the heating assembly of FIG. 1.

FIG. 16 illustrates a heating assembly 12m in some embodiments of the present disclosure. A width of a sheet heating portion of a heating element 122m is equal to a depth of a receiving groove 1210m, when the sheet heating portion of the heating element 122m is received in the receiving groove 1210m along a width direction, a top surface of the sheet heating portion is flush with an atomizing surface 1211m. As an alternative solution for the heating assembly 12 mentioned above, it is different from the heating assembly 12 mainly in that a liquid adsorbing surface 1212m is in a concave arc shape.

Figure 17:
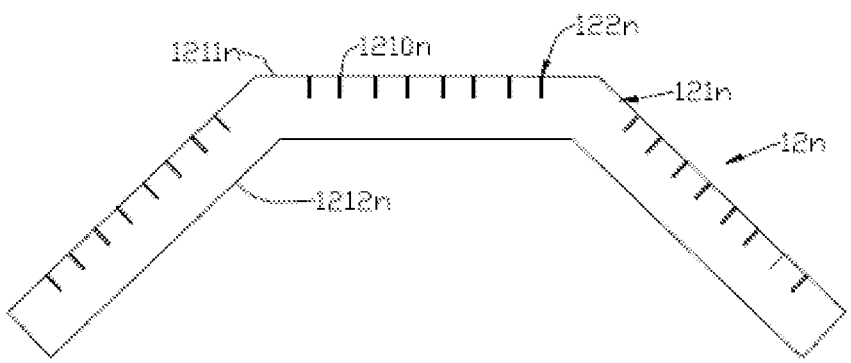
FIG. 17 is a schematic longitudinal sectional view of a thirteenth alternative solution of the heating assembly of FIG. 1.

FIG. 17 illustrates a heating assembly 12n in some embodiments of the present disclosure. As an alternative solution for the heating assembly 12 mentioned above, it is different mainly in that, as an alternative solution for the heating assembly 12 mentioned above, a porous body 121n of the heating assembly 12n includes three atomizing surfaces 1211n and three liquid adsorbing surfaces 1212n. Each atomizing surface 1211n corresponds to a sheet heating portion of one heating element 122n, and a width of the sheet heating portion of each heating element 122n is equal to a depth of a corresponding receiving groove 1210n. When the sheet heating portion of the heating element 122n is received in the receiving groove 1210n along a width direction, a top surface of the sheet heating portion is flush with the atomizing surface 1211n. Each liquid adsorbing surface 1212n is parallel to the corresponding atomizing surface 1211n. It can be understood that the number of the atomizing surfaces 1211n can also be two or more than three.

Figure 18:
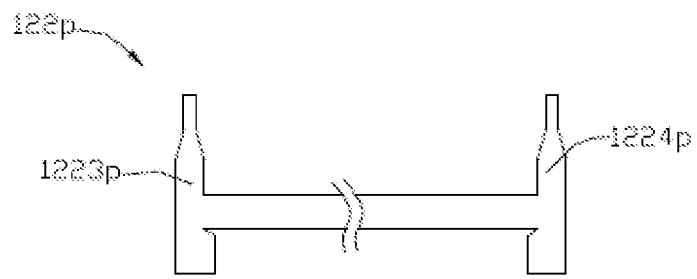
FIG. 18 is a schematic view of a first alternative solution of a heating element of the heating assembly of FIG. 1.

FIG. 18 illustrates a sheet heating portion of a heating element 122p in some embodiments of the present disclosure. As an alternative solution for the heating element 122 of the heating assembly 12 mentioned above, it is different mainly in that the heating element 122p includes an elongated sheet heating portion in the middle and two electrical connecting portions 1223p, 1224p connected to both ends of the heating portion, respectively. Instead of being bent into a specific shape, the elongated sheet heating portion as shown in the figure is in the shape of a strip. In some embodiments, the heating portion is integrally formed with the two electrical connecting portions 1223p, 1224p, and lower portions of the two electrical connecting portions 1223p, 1224p protrude from a lower edge of the heating portion, respectively, such that when the sheet heating portion of the heating element 122p is inserted into a porous body, the two electrical connecting portions 1223p, 1224p can be inserted more deeply to be engaged with the porous body more firmly to avoid the loosening caused by pulling of lead wires. Upper portions of the two electrical connecting portions 1223p, 1224p protrude from an upper edge of the heating portion, respectively, to act as electrical lead wires.

Figure 19:
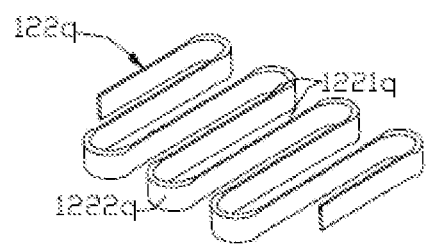
FIG. 19 is a schematic view of a second alternative solution of the heating element of the heating assembly of FIG. 1.

FIG. 19 illustrates a sheet heating portion of a heating element 122q in some embodiments of the present disclosure. The sheet heating portion of the heating element 122q is provided in an S-shaped long strip shape, which includes a plurality of flat portions 1221q parallel to each other and a plurality of bending portions 1222q connecting the flat portions 1221q in series. As an alternative solution for the sheet heating portion of the heating element 122 of the heating assembly 12 mentioned above, it is different mainly in that a thickness of the bending portion 1222q of the sheet heating portion of the heating element 122q is greater than a thickness of the flat portion 1221q thereof, so that a resistance of the bending portion 1222q is reduced, and thus the heat accumulation generated at the bending portion 1222q can be reduced. In some embodiments, the bending portion 1222q can also be widened to reduce the resistance at the corners. It can be understood that the solution is not limited to the sheet heating portion, a heating wire and a coated sheet heating element can also be applied. Specifically, when the heating wire has a flat portion and a bending portion, the bending portion can be designed to be larger directly, while for the coated heating element, the coat on the bending portion can be made thicker or wider.

Figure 20:
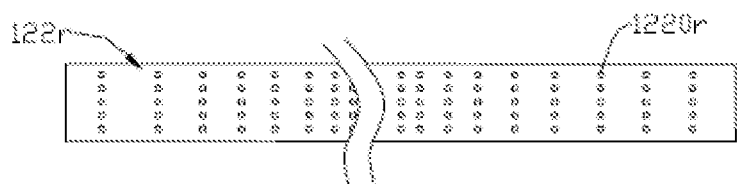
FIG. 20 is a schematic view of a third alternative solution of the heating element of the heating assembly of FIG. 1.

FIG. 20 illustrates a sheet heating portion of a heating element 122r in some embodiments of the present disclosure. As an alternative solution for the sheet heating portion of the heating element 122 mentioned above, it is different mainly in that the sheet heating portion of the heating element 122r is provided with a plurality of through holes 1220r extending through the thickness direction thereof. In a length direction of the sheet heating portion of the heating element 122r, a density of the through holes 1220r in the middle is greater than that of the through holes at both ends. As a result, in the length direction, a resistance of the sheet heating portion of the heating element 122r in the middle is greater than that of the sheet heating portion at both ends to meet requirements of specific heating assemblies and allow the distribution of the heat in the porous body to meet specific requirements.

Figure 21:
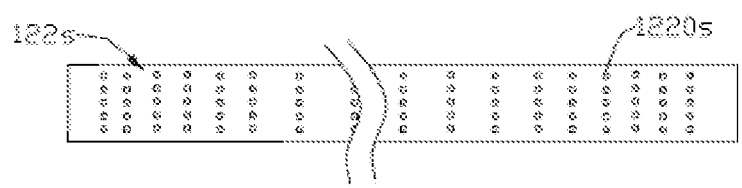
FIG. 21 is a schematic view of a fourth alternative solution of the heating element of the heating assembly of FIG. 1.

FIG. 21 illustrates a sheet heating portion of a heating element 122s in some embodiments of the present disclosure. As an alternative solution for the sheet heating portion of the heating element 122 mentioned above, it is different mainly in that the sheet heating portion of the heating element 122s is provided with a plurality of through holes 1220s extending through the thickness direction thereof. In a length direction of the sheet heating portion of the heating element 122s, a density of the through holes 1220r in the middle is lower than that of the through holes at both ends. As a result, in the length direction, a resistance of the sheet heating portion of the heating element 122r in the middle is lower than that of the sheet heating portion at both ends to meet requirements of specific heating assemblies.

Figure 22:
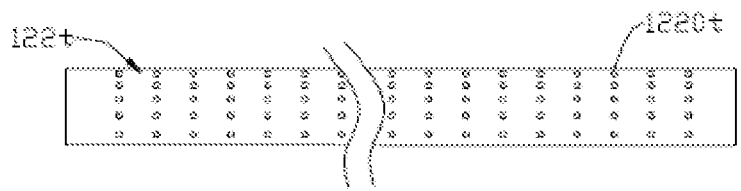
FIG. 22 is a schematic view of a fifth alternative solution of the heating element of the heating assembly of FIG. 1.

FIG. 22 illustrates a sheet heating portion of a heating element 122t in some embodiments of the present disclosure. As an alternative solution for the sheet heating portion of the heating element 122 mentioned above, it is different mainly in that the sheet heating portion of the heating element 122t is provided with a plurality of through holes 1220t extending through the thickness direction thereof. In a width direction of the sheet heating portion of the heating element 122t, a distribution density of the through holes 1220t gradually changes (for example, gradually increases or decreases) or changes stepwise. As a result, a resistance of the sheet heating portion of the heating element 122t gradually changes or changes stepwise in the width direction to meet the requirements of different heating assemblies.

Figure 23:
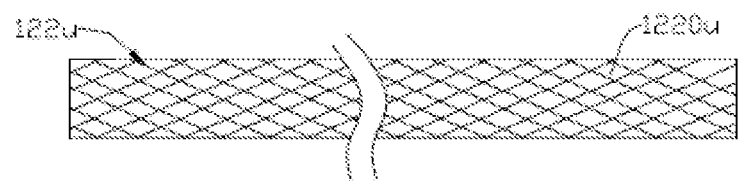
FIG. 23 is a schematic view of a sixth alternative solution of the heating element of the heating assembly of FIG. 1.

FIG. 23 illustrates a sheet heating portion of a heating element 122u in some embodiments of the present disclosure. As an alternative solution for the sheet heating portion of the heating element 122 mentioned above, it is different mainly in that, the sheet heating portion of the heating element 122u is a heating net which includes a plurality of meshes 1220u, the distribution of the meshes 1220u in a length direction of the sheet heating portion of the heating element 122u includes one of the following types: (1) the meshes are uniformly distributed, such that the resistance is uniformly distributed in the length direction; (2) the density of the meshes in the middle is lower than that of the meshes at both ends, and the density changes gradually or stepwise; (3) the density of the meshes in the middle is greater than that of the meshes at both ends, and the density changes gradually or stepwise. The distribution of the meshes 1220u in a width direction of the sheet heating portion of the heating element 122u includes one of the following types: (1) the meshes are uniformly distributed; (2) the density of the meshes on one side is greater than that of the meshes on another side, and the density changes gradually or stepwise.

Figure 24:
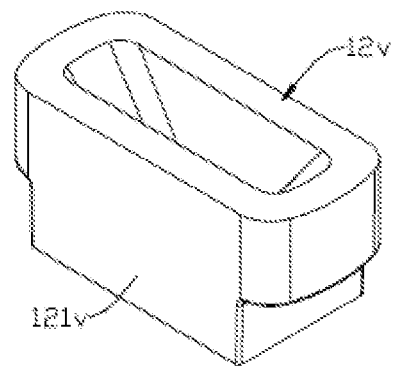
FIG. 24 is a schematic three-dimension view of a fourteenth alternative solution of the heating assembly of FIG. 1.
Figure 25:
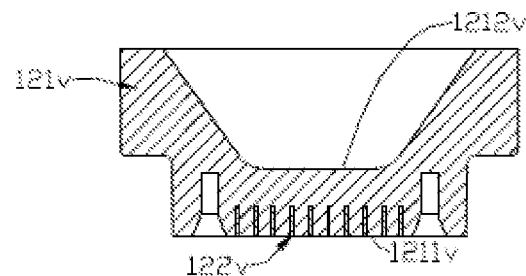
FIG. 25 is a schematic longitudinal sectional view of the heating assembly of FIG. 24.

FIG. 24 and FIG. 25 illustrate a heating assembly 12v in some embodiments of the present disclosure. As shown in the figures, the heating assembly 12v includes a porous body 121v and a sheet heating portion of a heating element 122v provided in the porous body 121v. As shown in the figures. As an alternative solution for the heating assembly 12 mentioned above, it is different mainly in that, a surface of a liquid adsorbing surface of the porous body 121v of the heating element 12v is recessed downwardly to form a groove 120v such that the whole porous body 121v is in the shape of a bowl, and an inner surface of a bottom wall of the porous body 121v forms a liquid adsorbing surface 1212v, while an outer surface of the bottom wall thereof forms an atomizing surface 1211v. The sheet heating portion of the heating element 122v is embedded in the atomizing surface 1211v. Since the porous body 121v is provided in the shape of a bowl, the whole porous body 121v is high enough to facilitate the mounting of the heating assembly 12v and the arrangement of a sealing sleeve 115. Besides, it is ensured that the distance from the liquid adsorbing surface 1212v to the atomizing surface 1211v is close enough to ensure the atomization effect while facilitating the mounting. The heating element 122v can be any one of the heating elements mentioned above.

Figure 26:
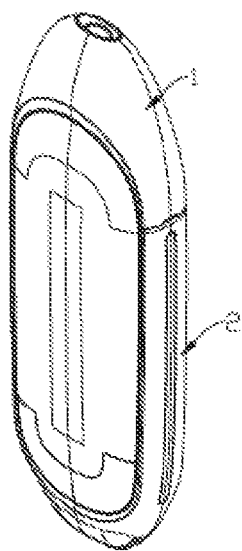
FIG. 26 is a schematic three-dimension assembled view of an electronic cigarette with the heating assembly of FIG. 24.
Figure 27:
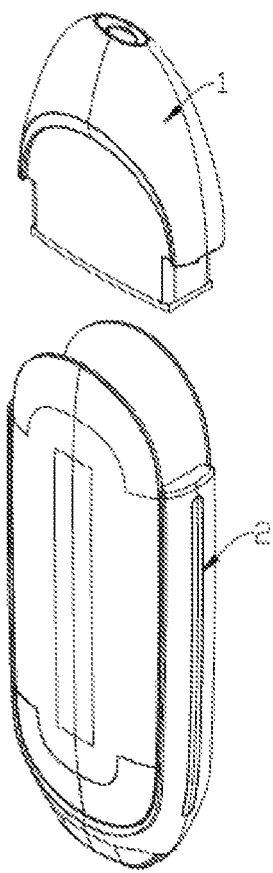
FIG. 27 is a schematic three-dimension exploded view of the electronic cigarette of FIG. 26.

FIG. 26 and FIG. 27 illustrate an electronic cigarette in some embodiments of the present disclosure. The heating assembly 12v shown in FIG. 24 and FIG. 25 is adopted in the electronic cigarette. It can be understood that any one of the heating assemblies mentioned above can also be adaptable to the electronic cigarette. In some embodiments, the electronic cigarette can be in a flat shape, which can include an atomizer 1 and a battery assembly 2 detachably connected to the atomizer 1. The atomizer 1 is configured for accommodating e-liquid and generating smoke. The battery assembly 2 is configured for supplying power for the atomizer 1. As shown in the figures, a lower end of the atomizer 1 is inserted into an upper end of the battery assembly 2, the atomizer 1 and the battery assembly 2 can be coupled together through magnetic attraction.

Figure 28:
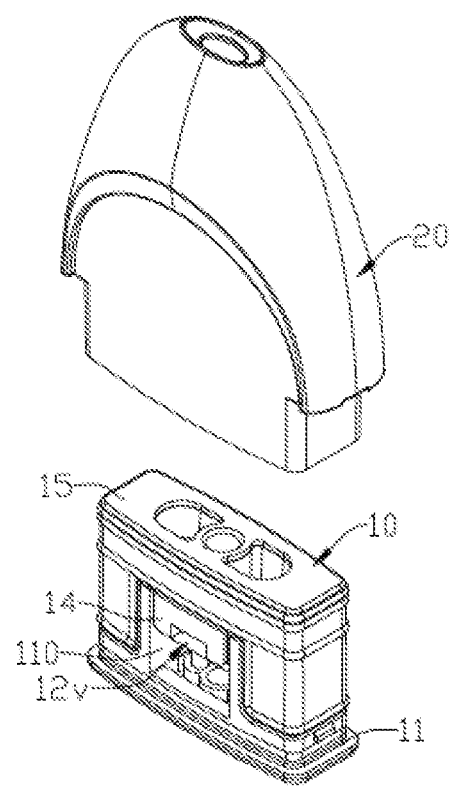
FIG. 28 is a schematic three-dimension exploded view of an atomizer of the electronic cigarette of FIG. 26.
Figure 29:
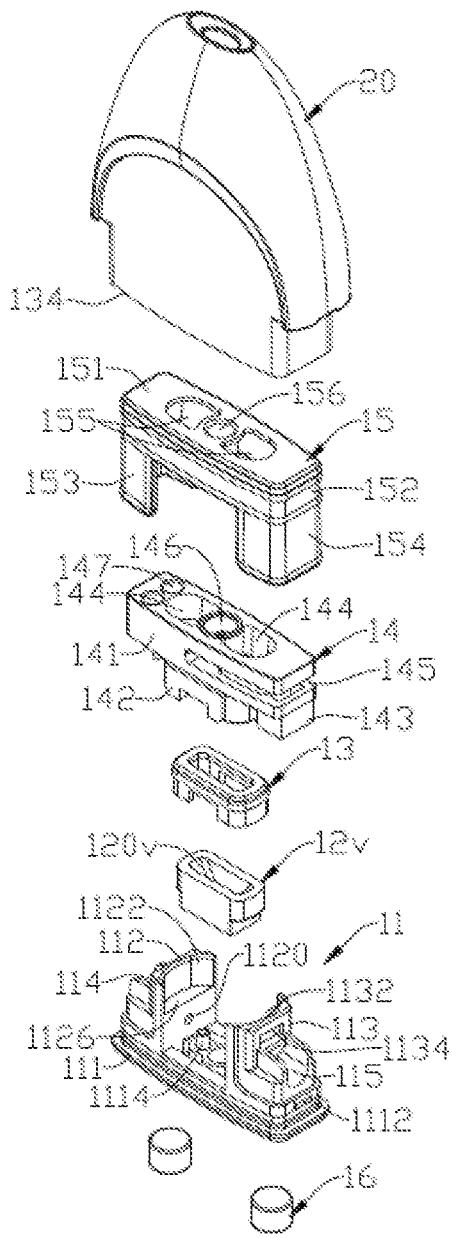
FIG. 29 is a further schematic three-dimension exploded view of the atomizer of the electronic cigarette of FIG. 26.
Figure 30:
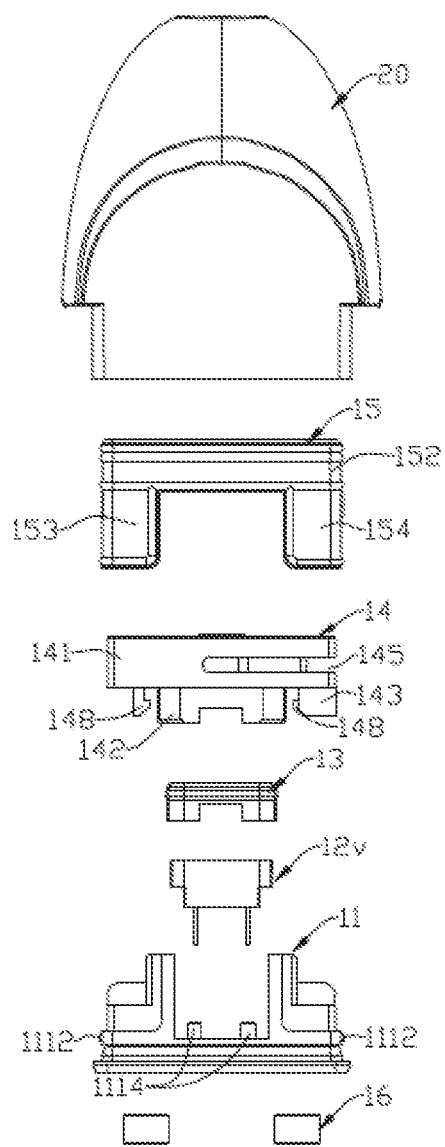
FIG. 30 is a schematic two-dimension exploded view of the atomizer of the electronic cigarette of FIG. 26.
Figure 31:
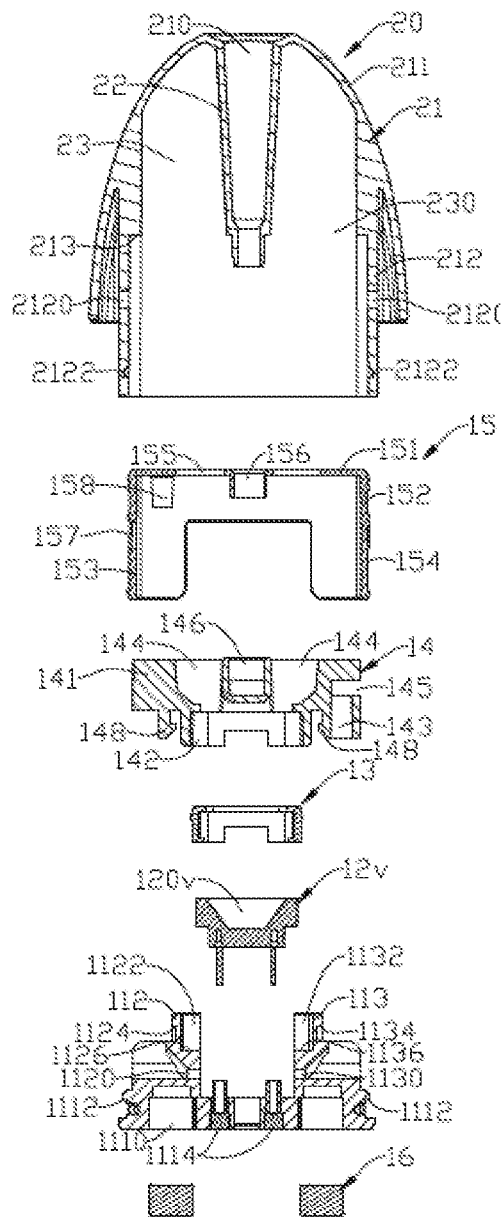
FIG. 31 is a schematic general cross-sectional exploded view of the atomizer of the electronic cigarette of FIG. 26.

As shown in FIG. 28, in some embodiments, the atomizer 1 can include an atomizing assembly 10 and a liquid storage device 20 sleeved on the atomizing assembly 10. The atomizing assembly 10 can be used to heat and atomize the e-liquid, while the liquid storage device 20 can be used to store the e-liquid to be supplied to the atomizing assembly 10.

Referring to FIG. 29 to FIG. 32 together, the atomizing assembly 10 includes a lower holder 11, the heating assembly 12v disposed on the lower holder 11, a sealing sleeve 13 sleeved on the heating assembly 12v, an upper holder 14 disposed on the lower holder 11 and abutted against the sealing sleeve 13, and a sleeve 15 sleeved on the upper holder 14. After the upper holder 14 abuts against the sealing sleeve 13, the heating assembly 12v is tightly clamped between the lower holder 11 and the upper holder 14. The presence of the sealing sleeve 13 can achieve the sealing between the heating assembly 12v and the upper holder 14 to prevent leakage of e-liquid and can also make the positioning of the heating assembly 12v in the horizontal direction more tightly.

In some embodiments, the lower holder 11 may include a base 111, a first supporting arm 112 standing on a top surface of the base 111, and a second supporting arm 113 standing on the top surface of the base 111 and disposed opposite to the first supporting arm 112. The heating assembly 12v is supported between the first supporting arm 112 and the second supporting arm 113, with the atomizing surface 1211v thereof facing the base 111 directly and spaced from the base 111 at an interval. The interval forms an atomizing cavity 110 to achieve the mixing of the smoke and the air.

In some embodiments, the base 111 can be in a shape of a rectangle plate. A bottom surface of the base 111 is recessed inwardly to form two receiving grooves 1110 for receiving two magnetic elements 16 therein, respectively. The magnetic elements 16 are used for magnetically attracting the atomizer 1 and the battery assembly 2 together. The base 111 is also provided with engaging hooks 1112 respectively on two opposite end surfaces thereof configured for engaging with the liquid storage device 20. The base 111 can also be provided with two electrode columns 1114 electrically connected to the heating assembly 12v on the bottom thereof, which are used to be electrically connected to positive and negative electrodes of the battery assembly 2, respectively.

In some embodiments, the first supporting arm 112 and the second supporting arm 113 can be in a shape of a plate. Inner side surfaces of the first supporting arm 112 and the second supporting arm 113 are respectively recessed to form accommodating grooves 1122, 1132 for an embedded portion 142 of the upper holder 14 to be embedded therein. The accommodating grooves 1122, 1132 are formed in upper half portions of the first supporting arm 112 and the second supporting arm 113, respectively; and steps 1126, 1136 are formed on the first supporting arm 112 and the second supporting arm 113, respectively. Both ends of the heating assembly 12v are supported on the steps 1126, 1136, respectively. Outer sides of top ends of the first supporting arm 112 and the second supporting arm 113 are further provided with engaging portions 1124, 1134 for engaging with the upper holder 14, respectively. In some embodiments, the first supporting arm 112 and the second supporting arm 113 are left-right symmetrically arranged to facilitate the assembly, that is, there is no need for an operator to distinguish beforehand which is the left end and which is the right end during the assembly.

In some embodiments, the lower holder 11 can also include a U-shaped air inlet groove structure 114 and a U-shaped air outlet groove structure 115. The air inlet groove structure 114 and the air outlet groove structure 115 are connected to outer sides of the first supporting arm 112 and the second supporting arm 113, respectively, and extend outwards horizontally. A through hole 1120 providing communication between the air inlet groove structure 114 and the atomizing cavity 110 is formed on the first supporting arm 112, while a through hole 1130 providing communication between the air outlet groove structure 115 and the atomizing cavity 110 is formed on the second supporting arm 113, so as to introduce air to carry away the smoke in the atomizing cavity 110. The through holes 1120, 1130 are located under the accommodating grooves 1122, 1132, respectively.

In some embodiments, the upper holder 14 can include a main body portion 141 having a substantially rectangular parallelepiped shape, the embedded portion 142 extending downwards from the middle of a bottom surface of the main body portion 141, and a second air inlet channel 143 extending downwards from the right end of the bottom surface of the main body portion 141. The embedded portion 142 is annular, and is accommodated in the accommodating grooves 1122, 1132 between the first supporting arm 112 and the second supporting arm 113 of the lower holder 111, and is sleeved on the periphery of the sealing sleeve 13. The upper holder 14 further includes two liquid channels 144 extending from the top surface to the bottom surface of the main body portion 141, a slot channel 145 formed on a side wall and surrounding the liquid channel 144 on the right side and in communication with the second air inlet channel 143, and a second air outlet channel 146 in communication with the slot channel 145. The second air outlet channel 146 extends through to be in communication with the slot channel 145 from the middle of the top surface of the upper holder 14. The left end of the top surface of the upper holder 14 is also recessed downwardly to form two positioning holes 147 to cooperate with the sleeve 15, thereby playing the functions of positioning and fool proofing. The upper holder 14 also includes an engaging hook 148 extending downwardly to be hooked onto the lower holder 11.

In some embodiments, the sleeve 15 can be a silicone sleeve, which can include a top wall 151, an annular first blocking wall 152 extending downwards from a periphery of the top wall 151, and two U-shaped second blocking walls 153, 154 extending downwards respectively from two ends of the first blocking wall 152. Two liquid inlet holes 155 and a sleeve air outlet channel 156 are formed on the top wall 151. The two liquid inlet holes 155 correspond to the two liquid channels 144 of the upper holder 14, respectively. The sleeve air outlet channel 156 is inserted into the second air outlet channel 146 of the upper holder 14 and is in communication with the second air outlet channel 146. The first blocking wall 152 is used to enclose the side wall of the main body portion 141 of the upper holder 112 and cover the slot channel 145 on the side wall to form an air-tight annular connecting channel for the upper holder. The second blocking walls 153, 154 cover the air inlet groove structure 1114 and the air outlet groove structure 1115 of the lower holder 111, respectively, and form an air-tight first air inlet channel and an air-tight first air outlet channel respectively together with the first supporting arm 1112 and the second supporting arm 115. A first air inlet hole 157 is formed on the second blocking wall 153 located on the left side, the first air inlet hole 157 is configured to be in communication with the external environment to introduce air into the first air inlet channel. The first air outlet channel is in communication with the second air inlet channel 143. Two positioning columns 158 extend downwards from the left end of the bottom surface of the top wall 151 of the sleeve 15 to respectively cooperate with the two positioning holes 147 of the upper holder 14, mainly to allow the first air inlet hole 157 located on the left side of the sleeve 15 to be precisely located on the left side of the assembly of the upper holder 112 and the lower holder 111, so as to ensure that the first air inlet hole 157 is in communication with the first air inlet channel, thereby playing the function of fool proofing.

The liquid storage device 20 includes a housing 21 provided with an air outlet 210, and an airflow tube 22 disposed in the housing 21 and in communication with the air outlet 210. The housing 21 includes a liquid storage portion 211 and a sleeve portion 212 connected to the liquid storage portion 211. A liquid storage cavity 23 is formed between the liquid storage portion 211 and the airflow tube 22. The liquid storage cavity 23 includes a liquid outlet 230, and the sleeve portion 212 is connected to a periphery of the liquid outlet 230 to be tightly sleeved on the atomizing assembly 10. A step 213 is formed between an inner wall surface of the sleeve portion 212 and an inner wall surface of the liquid storage portion 211. The step 213 abuts against the top surface of the atomizing assembly 10. In some embodiments, the sleeve portion 212 is integrally formed with the liquid storage portion 211. The air outlet 210 can be provided to be a suction nozzle in the shape of a flat trumpet.

The airflow tube 22 extends from the air outlet 210 towards the liquid outlet 230, with a distal end thereof extending into the sleeve portion 212 and inserted into the air outlet channel 156 of the sleeve 15, so as to be in communication with the second air outlet channel 146. The sleeve portion 212 is further provided with second air inlet holes 2120 on the left and right sides thereof, wherein the second air inlet hole 2120 on the left side is in communication with the first air inlet hole 157 of the sleeve 15, so that the air outside the housing 21 can enter the first air inlet channel which is formed by the sleeve 15 and the lower holder 11. Preferably, the housing 21 is symmetrically arranged as a whole to facilitate the assembling, because if there is only one side provided with the second air inlet hole 2120, workers have to perform an additional step of judging whether the second air inlet holes 2120 are located on the same side as the first air inlet hole 157 during assembling. Engaging slots 2122 are formed in inner walls of the left and right sides of the sleeve portion 212 to cooperate with the engaging hooks 1112 of the lower holder 11, respectively, so that the housing 21 and the lower holder 111 can be easily engaged together.

When the atomizer 1 is assembled, the following steps can be used:
(1) the sealing sleeve 13 is first sleeved on the heating assembly 12v;
(2) the assembly of the sealing sleeve 13 and the heating assembly 12v is inserted into the embedded portion 142 of the upper holder 14;
(3) the upper holder 14 is then covered on the lower holder 11 to allow the engaging hook 148 of the heating assembly of the upper holder 14 to be engaged with the engaging portions 1124, 1134 of the lower holder 11, such that the upper holder 14 is engaged to the lower holder 11; and the electrode lead wires of the heating assembly 12v is electrically connected to the electrode columns 1114 on the lower holder 11;
(4) the sleeve 15 is then sleeved on the upper holder 14 to finish the assembling of the atomizing assembly 10; and
(5) the atomizing assembly 10 is inserted from below into the sleeving portion 212 of the liquid storage device 20 filled with the e-liquid, so that the top surface thereof abuts against the step 213 to block the liquid outlet 230 of the liquid storage cavity 23, and the engaging hooks 1112 of the lower holder 11 are engaged into the engaging slots 2122 of the sleeve portion 212 to achieve the assembling of the atomizer 1, which is convenient and quick.

Figure 32:
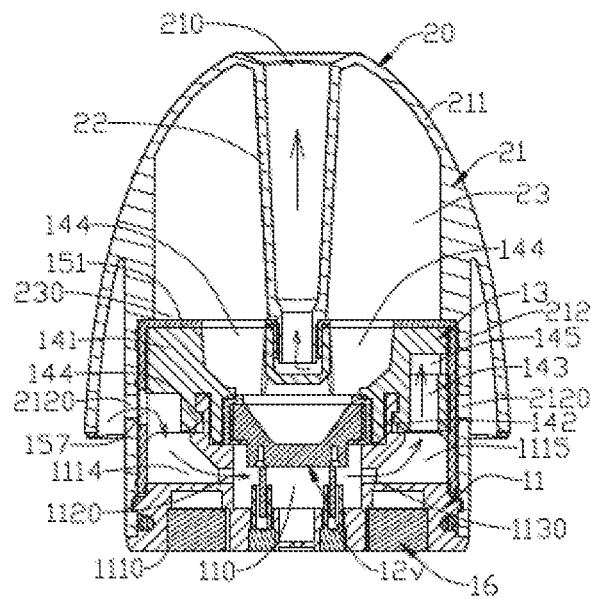
FIG. 32 is a schematic longitudinal sectional assembled view of the atomizer of the electronic cigarette of FIG. 26.

As a result, the flow path of the air in the atomizer 1 is shown by the arrow in FIG. 32: the air first flows into the first air inlet channel through the second air inlet hole 2120 and the first air inlet hole 157, and then flows into the atomizing cavity 110 through the through hole 1120 to be mixed with the smoke. The mixture of smoke and air flows into the first air outlet channel through the through hole 1130 and then flows into the second air inlet channel 143. The mixture of smoke and air then flows into the annular connecting channel for the upper holder and flows into the second air outlet channel 1466. The mixture of smoke and air finally flows into the airflow tube 22, and is finally exhausted out of the atomizer 1 through the air outlet 210. The e-liquid in the liquid storage cavity 23 flows sequentially through the liquid inlet hole 155 of the sleeve 15 and the liquid channel 144 of the upper holder 14, and then flows into the groove 120 of the heating assembly 12v to be in contact with the liquid adsorbing surface 1212v, thereby achieving the delivery of the e-liquid.

In some embodiments, the location of the second air inlet hole 2120 is higher than that of the atomizing cavity 110, which can better prevent the leakage of the e-liquid from the second air inlet hole 2120 in a normal use state. The bottom of the whole airflow tube of the atomizer 1 is substantially U-shaped. The direction of the airflow at the atomizing cavity 110 is parallel to the atomizing surface 1211v of the heating assembly 12v, so that the smoke atomized at the atomizing surface 1211v can be carried away more easily.

In some embodiments, the porous body 121v of the heating assembly 12v has a groove on the top surface thereof. After the e-liquid enters the groove, the efficiency of liquid guiding can be increased. Specifically, on the one hand, the arrangement of the groove increases the contact area between the porous body and the e-liquid; on the other hand, the distance between the bottom surface of the groove and the outer surface of the bottom of the porous body 121v is very small, which can reduce the flow resistance of the e-liquid reaching the outer surface of the bottom of the porous body 121v. In addition, since the liquid guiding side surface of the heating element 12v needs to be sealed by the sealing sleeve 115 to seal the e-liquid to prevent the e-liquid from flowing into the atomizing cavity 110, the porous body 121v needs to have a certain height to meet the requirements of the arrangement of the sealing element and the rigidity requirement of the porous body 121v itself. By arranging the above-mentioned groove, both the thickness requirement of the porous ceramic body and the requirement of liquid guiding efficiency can be met.

It can be understood that the heating assembly 12v of the electronic cigarette mentioned above can also use other suitable heating assemblies. The heating portion of the heating element 122v is not limited to be in the shape of an elongated sheet, it can also be in other shapes such as a filament and so on.

Figure 33:
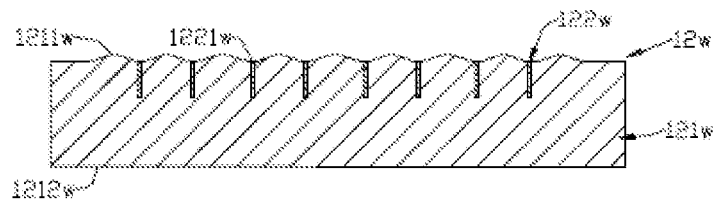
FIG. 33 is a schematic three-dimension view of a fifteenth alternative solution of the heating assembly of FIG. 1.

FIG. 33 illustrates a heating assembly 12w in some embodiments of the present disclosure. As an alternative solution of the heating assembly 12 mentioned above, it is different mainly in that, a porous body 121w of the heating assembly 12w includes a wave-shaped atomizing surface 1211w, and flat portions 1221w of a sheet heating portion of a heating element 122w are respectively disposed corresponding to troughs of the wave-shaped atomizing surface 1211w and are perpendicular to a plane where the wave-shaped atomizing surface 1211w is located, thereby reducing the dry burning effect through the e-liquid accumulated at the troughs.

Figure 34:
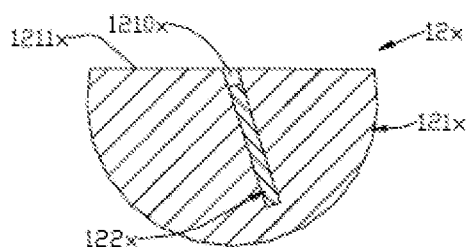
FIG. 34 is a schematic three-dimension view of a sixteenth alternative solution of the heating assembly of FIG. 1.

FIG. 34 illustrates a heating assembly 12x in some embodiments of the present disclosure. A width of a sheet heating portion of a heating element 122x of the heating assembly 12x is smaller than a depth of a receiving groove 1210x. Therefore, when the sheet heating portion of the heating element 122x is received in the receiving groove 1210x in a width direction, a top surface thereof is lower than an atomizing surface 1211x. As an alternative solution for the heating assembly 12a mentioned above, it is different mainly in that an angle is formed between the width direction of the sheet heating portion of the heating element 122x of the heating assembly 12x and a normal direction of the atomizing surface 1211x. Preferably, the angle is smaller than 20 degrees.

Figure 35:
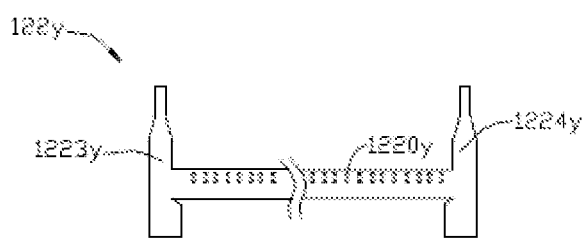
FIG. 35 is a schematic view of a first alternative solution of the heating element of the heating assembly of FIG. 18.

FIG. 35 illustrates a heating element 122y in some embodiments of the present disclosure. The heating element 122y includes a strip-shaped heating portion in the middle and two electrical connecting portions 1223y, 1224y respectively integrally connected to two ends of the heating portion. As an alternative solution for the heating element 122p mentioned above, it is different mainly in that, the sheet heating portion of the heating element 122y is provided with a plurality of through holes or blind holes 1220y at positions adjacent to an atomizing surface of a porous body to improve the resistance of the area.

Figure 36:
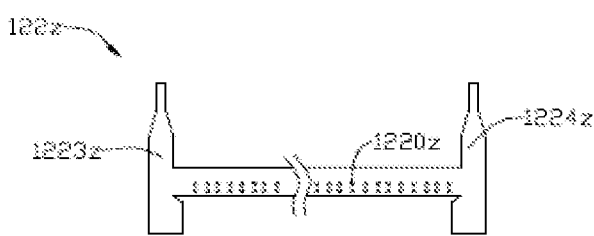
FIG. 36 is a schematic view of a second alternative solution of the heating element of the heating assembly of FIG. 18.

FIG. 36 illustrates a heating element 122z in some embodiments of the present disclosure. The heating element 122z includes an elongated sheet heating portion in the middle and two electrical connecting portions 1223z, 1224z respectively integrally connected to two ends of the heating portion. As an alternative solution for the heating element 122p mentioned above, it is different mainly in that, the heating portion of the heating element 122z is provided with a plurality of through holes or blind holes 1220z at positions away from an atomizing surface of a porous body to improve the resistance of the area.

It can be understood that although the difference between the alternative solutions of the heating element and the porous body in the above mentioned embodiments and those in the aforementioned embodiments are mainly described, they can be replaced by each other as long as they are not contradictory. For example, the heating element in any embodiment above mentioned can cooperate with the porous body in any embodiment, and any heating assembly above mentioned can be applied to the electronic cigarette.

What mentioned above are merely the embodiments of the present disclosure, and will not limit the patent scope of the present disclosure consequently. Any equivalent structure or equivalent transformation of the procedure made using the specification and the accompanying drawings of the present disclosure, or direct or indirect applying thereof to other relevant technical fields, are all within the patent protection scope of the present disclosure for the same reason.

What is claimed is:

1. A heating assembly of an electronic cigarette, the heating assembly comprising:
    a porous body configured for adsorbing e-liquid; and
    at least one heating element configured for heating and atomizing the e-liquid adsorbed into the porous body;
    wherein the at least one heating element comprises an elongated sheet heating portion, wherein the sheet heating portion comprises a heating net, and at least partial section of the heating net is at least partially embedded in the porous body, and the porous body comprises an atomizing surface corresponding to the at least partial section.

2. The heating assembly of the electronic cigarette according to claim 1, wherein a density of meshes of the at least partial section in a length direction is less in the middle and greater at both sides, and changes gradually or stepwise.

3. The heating assembly of the electronic cigarette according to claim 1, wherein a density of meshes of the at least partial section in a length direction is greater in the middle and less at both sides, and changes gradually or stepwise.

4. The heating assembly of the electronic cigarette according to claim 1, wherein a density of meshes of the at least partial section in a width direction is less at one side and greater at the other side, and changes gradually or stepwise.

5. The heating assembly of the electronic cigarette according to claim 1, wherein the at least partial section is embedded in the porous body in a manner that a movement direction of at least one of the e-liquid and smoke in the porous body follows along a width direction of the at least partial section.

6. The heating assembly of the electronic cigarette according to claim 1, wherein the at least partial section in the width direction of the at least partial section is substantially perpendicular to a plane where the atomizing surface is located.

7. The heating assembly of the electronic cigarette according to claim 1, wherein the at least partial section extends in a length direction of the at least partial section along a direction parallel to a plane where the atomizing surface is located.

8. The heating assembly of the electronic cigarette according to claim 1, wherein the porous body comprises a receiving groove adapted to the at least partial section, the receiving groove is formed on the atomizing surface, and a depth direction of the receiving groove is substantially perpendicular to a plane where the atomizing surface is located.

9. The heating assembly of the electronic cigarette according to claim 1, wherein two opposite surfaces of the at least partial section defined by length and width are in direct contact with the porous body.

10. The heating assembly of the electronic cigarette according to claim 1, wherein the at least partial section comprises a plurality of flat portions parallel to each other and a plurality of bending portions sequentially connecting the plurality of flat portions in series, the atomizing surface is provided in a wavy shape, and the plurality of flat portions are disposed corresponding to troughs of the atomizing surface, respectively.

11. The heating assembly of the electronic cigarette according to claim 1, wherein the porous body comprises a first layer adjacent to the atomizing surface and a second layer away from the atomizing surface, wherein a thermal conductivity of the first layer is greater than that of the second layer.

12. The heating assembly of the electronic cigarette according to claim 11, wherein the at least partial section is embedded in the first layer.

13. The heating assembly of the electronic cigarette according to claim 1, wherein a thermal conductivity of the porous body gradually increases in a direction from an area away from the atomizing surface to an area adjacent to the atomizing surface.

14. The heating assembly of the electronic cigarette according to claim 13, wherein the at least partial section is adjacent to the atomizing surface.

15. The heating assembly of the electronic cigarette according to claim 1, wherein the at least partial section is integrally embedded in the porous body.

16. The heating assembly of the electronic cigarette according to claim 1, wherein the at least one heating element comprises two electrical connecting portions integrally connected to both ends of the sheet heating portion, respectively; each of the electrical connecting portions comprises a lower portion protruding from a lower edge of the sheet heating portion and an upper portion protruding from an upper edge of the sheet heating portion.

17. An electronic cigarette, comprising the heating assembly of the electronic cigarette of claim 1.

18. The heating assembly of the electronic cigarette according to claim 1, wherein the porous body comprises a sintered porous body, the at least partial section is integrally formed with the sintered porous body by sintering.

19. A heating assembly of an electronic cigarette the heating assembly comprising:
    a porous body configured for adsorbing e-liquid; and
    at least one heating element configured for heating and atomizing the e-liquid adsorbed into the porous body;
    wherein the at least one heating element comprises an elongated sheet heating portion, wherein the sheet heating portion comprises a heating net, and at least partial section of the heating net is at least partially embedded in the porous body, and the porous body comprises an atomizing surface corresponding to the at least partial section;
    wherein the porous body comprises a receiving groove adapted to the at least partial section, the receiving groove is formed on the atomizing surface, and a depth direction of the receiving groove is substantially perpendicular to a plane where the atomizing surface is located; and wherein the at least partial section is received in the receiving groove, and a top surface of the at least partial section is flush with the atomizing surface, or the top surface of the at least partial section is lower than the atomizing surface, or the top surface of the at least partial section protrudes from the atomizing surface.

20. The A heating assembly of an electronic cigarette according to claim 1, the heating assembly comprising:
- a porous body configured for adsorbing e-liquid; and
- at least one heating element configured for heating and atomizing the e-liquid adsorbed into the porous body;
- wherein the at least one heating element comprises an elongated sheet heating portion, wherein the sheet heating portion comprises a heating net, and at least partial section of the heating net is at least partially embedded in the porous body, and the porous body comprises an atomizing surface corresponding to the at least partial section; and
- wherein the at least partial section comprises a plurality of flat portions parallel to each other and a plurality of bending portions sequentially connecting the plurality of flat portions in series, the flat portions are arranged at intervals in a direction parallel to a plane where the atomizing surface is located, and the intervals are larger in the middle and smaller at both sides, or smaller in the middle and larger at the both sides.

* * * * *